United States Patent [19]
Arndt et al.

[11] Patent Number: 5,167,499
[45] Date of Patent: Dec. 1, 1992

[54] NI-TI ORTHODONTIC PALATAL EXPANSION ARCH

[76] Inventors: Wendell V. Arndt, 26650 W. 143rd St., Olathe, Kans. 66061; Carl J. Berendt, 2612 Via Masda, Carlsbad, Calif. 92008

[21] Appl. No.: 662,204

[22] Filed: Feb. 27, 1991

[51] Int. Cl.$^5$ ................................................ A61C 3/00
[52] U.S. Cl. ........................................ 433/7; 433/18; 433/20
[58] Field of Search ............... 433/6, 7, 18, 20, 22, 433/24

[56] References Cited

U.S. PATENT DOCUMENTS

| | | | |
|---|---|---|---|
| 1,395,922 | 11/1921 | McCarter | 433/20 X |
| 1,471,785 | 10/1923 | Fernald | 433/20 X |
| 1,582,570 | 4/1926 | Brust | 433/7 |
| 4,412,819 | 11/1983 | Cannon | 433/20 |
| 4,479,779 | 10/1984 | Wool | 433/20 |
| 4,571,179 | 2/1986 | Balenseifen | 433/20 X |
| 4,592,725 | 6/1986 | Goshgarian | 433/7 |
| 4,815,968 | 3/1989 | Keller | 433/7 |
| 4,818,226 | 4/1989 | Berendt et al. | 433/20 |
| 4,900,251 | 2/1990 | Andreasen | 433/20 |
| 4,976,614 | 12/1990 | Tepper | 433/6 X |
| 5,017,133 | 5/1991 | Miura | 433/20 |
| 5,018,969 | 5/1991 | Andreiko et al. | 433/20 |
| 5,044,947 | 9/1991 | Sachdeva et al. | 433/18 X |
| 5,046,948 | 9/1991 | Miura | 433/18 X |
| 5,080,584 | 1/1992 | Karabin | 433/20 |

*Primary Examiner*—Cary E. O'Connor
*Assistant Examiner*—Nicholas D. Lucchesi
*Attorney, Agent, or Firm*—Richard P. Stitt; Chase & Yakimo

[57] ABSTRACT

A removable orthodontic palatal expansion arch having a generally "M"-shaped configuration, the arch having a center segment composed of a near-stoichiometric alloy of nickel and titanium which possesses memory-retaining characteristics to simultaneously expand the bicuspids and expand, rotate, intrude and/or torque the maxillary molars, and end segments composed of an alloy of stainless steel or another biocompatible material configured for securing the archwire to lingual sheaths attached to molar bands.

2 Claims, 2 Drawing Sheets

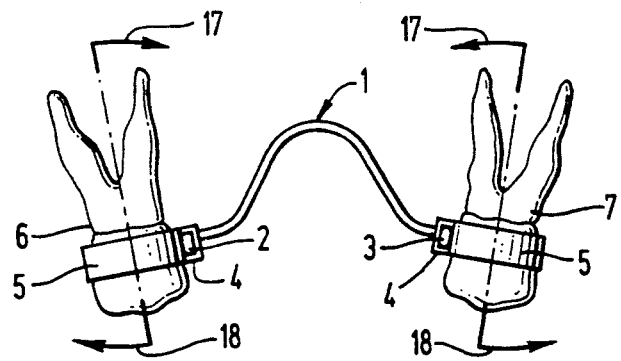
FIG. 5
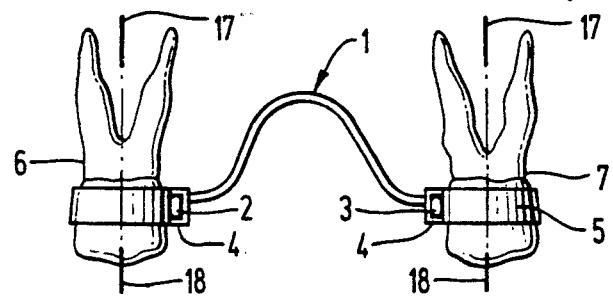
FIG. 6
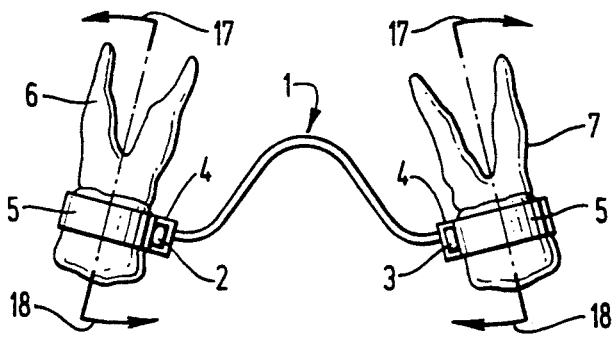
FIG. 7
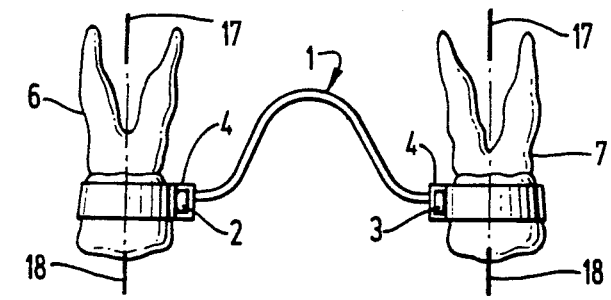
FIG. 8
FIG. 9    FIG. 9A
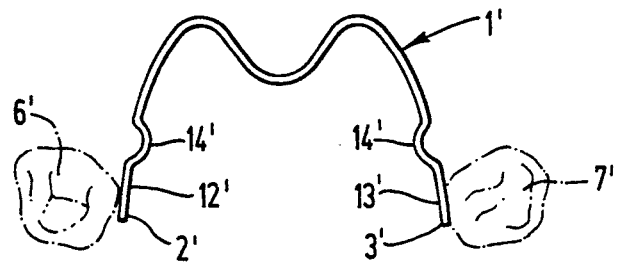 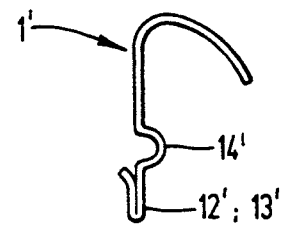

NI-TI ORTHODONTIC PALATAL EXPANSION ARCH

BACKGROUND OF THE INVENTION

The invention relates generally to a nickel-titanium palatal expansion arch having a generally "M-shaped" configuration for simultaneous expansion of the bicuspids and expansion, rotation, torquing or intruding of the maxillary molars.

Maxillary palatal expansion appliances have been used by orthodontists for many years to create additional room for developing permanent teeth and to correct aberrations of the first molar positions. Conventional orthodontic palatal expansion devices rely on jack screws, springs and heavy helix wires to accommodate the range of movement required by the clinician. The screw-type devices require patient involvement through the treatment period in which the patient is required to adjust a jack screw which is embedded in an acrylic palatal device. Spring devices are used with coiled springs placed between a sliding rod and sheath to deliver a low extended range force to the parallel planes which begin at and are attached to a welded band device affixed to the first molars. The rods or legs parallel the teeth toward the midline. The spring rod and sheath lie in place away from the palate, becoming an interference to occlusal functions. Examples of such prior art devices are found in U.S. Pat. Nos. 4,037,324 and 3,792,529.

Each prior art appliance was painstakingly crafted each time a new patient was treated since there were no commercially standardized appliances available in any of these configurations. Thus, the clinician was involved in the time-consuming making of the appliance for each patient. Whether the clinician utilized a soldered jack screw, helix or spring device, these appliances had a very limited ability to rotate, upright, or torque malaligned or biased first molars whose proper position is all important to the orthodontic treatment objectives. In each case, additional and sometimes complex procedures were necessary to complete the molar movement.

The 3-D quad helix prior art appliance consists of a 0.036 inch wire having a "W"-shaped four loop system, laser-welded to twin vertical posts which plug into vertical lingual sheaths affixed via spot welding to the first molars. The portion of the device in contact with the cuspids and bicuspids bilaterally are called extenders and have been reduced to 0.025 inch wire for increased flexibility. If upon insertion the molar is biased in any dimension from the normal, the appliance in turn is distorted in the way it is positioned on the palate, i.e., the extenders become skewed out over the tongue when the appliance is inserted in the malpositioned molars and irritates the tongue. The appliance is fabricated in different sizes so that the clinician can select the appropriate one for the patient.

Clinicians using the 3-D expansion arch see their patients at three to four week intervals, at which time the arch can be reactivated. New force moments can be incorporated into the archwire during each visit so there would be new forces imparted to continue the movement of the teeth to a desired position. Over the course of a few weeks, the round stainless steel 3-D archwire gradually loses its ability to impart force to the teeth so that at the end of the three or four-week period, it is necessary to remove and reshape the various components.

All of the forgoing described appliances with each activation produce very high initial pressure between the maxillary teeth and palatal suture producing pain and undesirable bone responses.

Vertical post appliances remain unpopular with orthodontists because they depend on a friction grip which is immediately put under strain by any activation of the appliance. The moment that any additional force from the tongue occurs, the two forces combine to dislodge the appliance. The laser welded posts impart strain into the extenders that makes even modest adjusting predisposed to breakage.

Another prior art removable appliance used to reciprocally rotate, expand, contract, intrude and/or torque the upper molars, but does not have the capability to expand the bicuspid segment, is disclosed in U.S. Pat. No. 3,792,529.

The prior art also includes U.S. Pat. No. 4,037,324, which discloses the use of an archwire having a specific chemical composition wire which causes the archwire to return to a preset shape or length after being deformed and then heated. The mechanical memory of the wire will tend to restore the wire to a preset shape upon heating in order to level or torque malposed teeth. The prior art wires are formed of a Nitonol alloy, which is a known near-stoichiometric alloy of nickel and titanium. The alloy may also include cobalt substituted for nickel on an atom-for-atom basis so that the composition is NiTi; CO: 0.935, 0.065.

SUMMARY OF THE INVENTION

The orthodontic archwire, according to the invention, is a pre-formed wire having a generally "M-shaped" configuration and is comprised of a near-stoichiometric alloy of nickel and titanium which possesses memory-retaining characteristics. The mid-point of the "M-shaped" archwire is centered with the mid-point of the palatal concavity near the two front anterior teeth and extends bilaterally along the palatal concavity to crimp tubes which unite segments composed of stainless steel or another bio-compatible material having length adjustment loops and ending in rectangular lingual sheath inserts. The archwire is connected to lingual sheaths mounted on the molars and adapted to receive the end portions of the archwire. The archwire, due to its memory-retaining characteristics, when stressed, will attempt to return to its pre-formed configuration, and in so doing will provide a low and continual force to the teeth, thereby moving the teeth to their desired location.

Two features of the present invention, prefabrication and removability, represent a giant step forward for clinicians. Since our invention is prefabricated, labor intensive laboratory procedures are eliminated in constructing an arch device for each patient. The removable feature makes it possible to control molar positions better than any previous device mentioned.

It is an object of the present invention to provide a removable pre-formed palatal expansion arch with memory-retaining characteristics to expand the bicuspid and molar segments bilaterally to a pre-determined shape in order to make more space for the anterior teeth and thereby permit the latter to assume their proper position in the maxillary arch.

It is a further object of the invention to provide removable palatal expansion arches that are prefabricated in several sizes having a specific configuration and which are comprised of a near-stoichiometric alloy of nickel and titanium so that after mounting in the lingual sheaths of the molars, the alloy will impart counter-moment forces to expand the bicuspids and rotate, expand, intrude, and/or torque the molars.

It is also an object of the invention to provide a removable maxillary palatal expansion arch that possesses a set mechanical characteristic with low constant mechanical forces at ambient and below mouth temperatures for ease of insertion, and would apply a greater sustained constant force when at mouth temperature through treatment until the desired change in palatal width and molar rotation is achieved.

These forces approximate the optimum, light continuous force described in the prior art for physiological expansion of the maxillary teeth and palatal suture.

It is another object of the invention to provide a removable palatal expansion arch which may be removed and adjusted by the clinician or at the manufacturer's laboratory to a different shape by a re-heat treating of the Ni-Ti segment while holding in a newly-formed shape.

It is another object of the invention to provide a removable palatal expansion arch of a specific configuration and composition so that the forces applied when in use are transmitted in parallel planes, mesial to distal, and can be regulated by different diameters of Ni-Ti wire.

It is still another object of the invention to provide a removable palatal expansion arch pre-formed so as not to exceed a desired palatal dimension at the end of treatment in order to prevent over expansion of the arch should the device be left in beyond the scheduled treatment.

It is another object of the invention to provide an improved orthodontic system for intermittently varying the load applied to promote orthodontic movement of teeth more effectively.

It is a further object of the invention to provide an improved orthodontic system wherein intermittently varying orthodontic loads are applied in response to the temperature of the patient's mouth.

Another object of the invention is to provide an improved method of promoting orthodontic movement of teeth.

A further object is to reduce tedious laboratory procedures and to reduce the pain engendered by the patient by application of other prior art devices having very high moment forces at the beginning of treatment.

These and other objects are not meant in a limiting sense and will be pointed out and described in further detail hereinafter.

BRIEF DESCRIPTION OF THE DRAWINGS

In the accompanying drawings, the same reference numerals designate the same or similar elements in all of the views:

FIG. 5 is a side elevational view of a patient's upper first permanent molars with attached sheaths biased inwardly. Insertion of the upright lingual sheath insert, produces a counter-moment force in the Ni-Ti wire, the counter-movement of which torques the tooth toward its proper position;

FIG. 6 is a side elevational view similar to FIG. 5, illustrating the upper first permanent molars after uprighting;

FIG. 7 is a side elevational view similar to FIG. 5, but showing patient's upper first permanent molars with attached sheath biased outwardly. Insertion of the upright lingual sheath insert produces a counter-moment force in the Ni-Ti wire, the counter-movement of which torques the tooth toward its proper position;

FIG. 8 is a side elevational view of the upper first permanent molars illustrated in FIG. 7 after said molars have been uprighted;

FIG. 9 is a plan view of one embodiment of the M-shaped Ni-Ti archwire wherein the entire archwire is composed of Ni-Ti; and FIG. 9A is a side view of the Ni-Ti palatal expansion arch of FIG. 9.

DETAILED DESCRIPTION OF THE PREFERRED EMBODIMENTS

Figure 1:
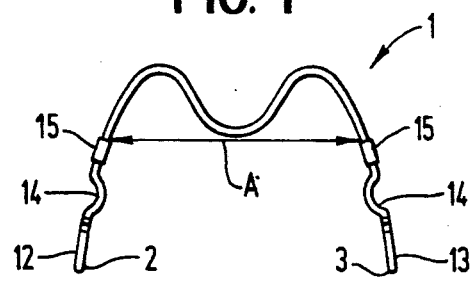
FIG. 1 is a plan view of the improved Ni-Ti palatal expansion arch.
Figure 1A:
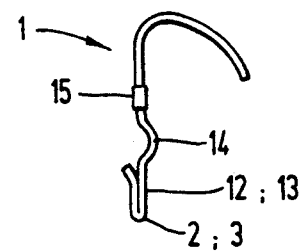
FIG. 1A is a side view of the Ni-Ti palatal expansion arch of FIG. 1.

Referring now particularly to FIGS. 1 and 1A of the drawings, illustrated therein is the removable Ni-Ti maxillary palatal expansion arch partially composed of a near-stoichiometric alloy of nickel and titanium extending bilaterally along the palatal concavity uniting end sections made from stainless steel and terminating with lingual sheath inserts. Archwire 1 is preferably made of a near-stoichiometric alloy of nickel and titanium having memory-retaining characteristics. As will be observed, archwire 1 is bent to provide a general "M-shape" which provides the counter-forces necessary for moving teeth as will be further described herein. Connected to archwire 1 is first stainless steel end 12. The stainless steel ends 12 and 13 have a pair of unitary length adjustment loops 14 and terminate with lingual sheath inserts 2, 3. The stainless steel ends 12 and 13 and adjustment loops 14 are united by crimp tubes 15 to the "M-shaped" Ni-Ti archwire 1.

Archwire 1 may be formed of 0.036 inch diameter nickel-titanium wire that is crimped to 0.036 inch diameter stainless steel which form end segments 12 and 13, although other equivalent materials and diameter sizes could be utilized and the invention is by no means meant to be limited in this respect.

In one embodiment of the invention, archwire 1 is provided in a variety of widths designated as line A, to fit each particular patient's palatal arch. The width dimension of line A is determined by the measurement in millimeters from the first bicuspid on one side of the maxillary arch and following the concavity of the palate transversely to the first bicuspid on the other side of the maxillary arch. For most purposes, four different archwire widths, such as 25, 30, 35 and 40 millimeters, will provide an adequate variety to accommodate the majority of patients. The width of the archwire is not a critical feature of the present invention due to the posterior adjustment loops. Thus, other dimensions relating to the archwire of line A are contemplated and the widths that are disclosed are not meant to be limiting, but are offered only as examples.

As appears in FIGS. 2-8, in the installation of archwire 1, on a patient's upper first permanent molars 6, 7, a metal band 5 is first fitted on and surrounds each of the molars. In accordance with the present invention, metal bands 5 are provided with lingually-projecting sheaths 4, fixed thereon by any conventional means such as brazing. Sheaths 4 are rectangular in cross-section and adapted to receive the end sections 12 and 13. In installing the Wire ends 12, 13, lingual sheath inserts 2, 3 are inserted into sheaths 4 and retained by a locking indent provided on the lingual sheath inserts or by another means known in the art. The lingual sheath inserts have a spring-like quality which causes wire ends 12 and 13 to be firmly retained in the sheaths. Moreover, with the wire end portions firmly retained within the sheaths, there is minimal twisting of the wire end portions within the sheaths, thereby promoting the torquing, expanding and rotating actions of the archwire. When it is desired to remove the arch wire, however, it is an easy matter to remove the wire ends from their retaining sheaths.

Figure 2:
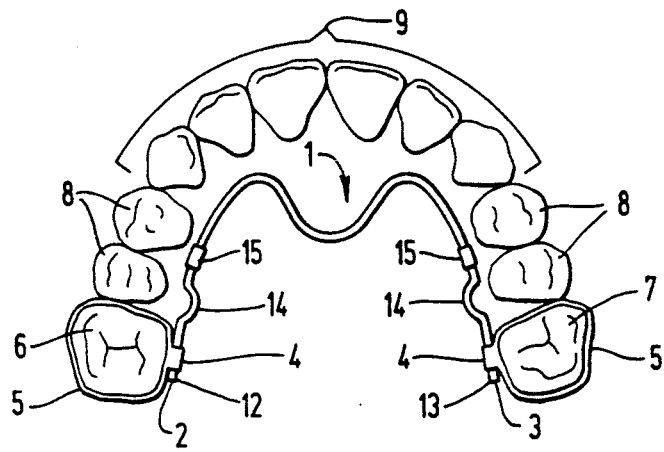
FIG. 2 is an inferior plan view of a maxillary dental arch showing the Ni-Ti palatal expansion archwire inserted in position on the patient's upper first permanent molar.
Figure 3:
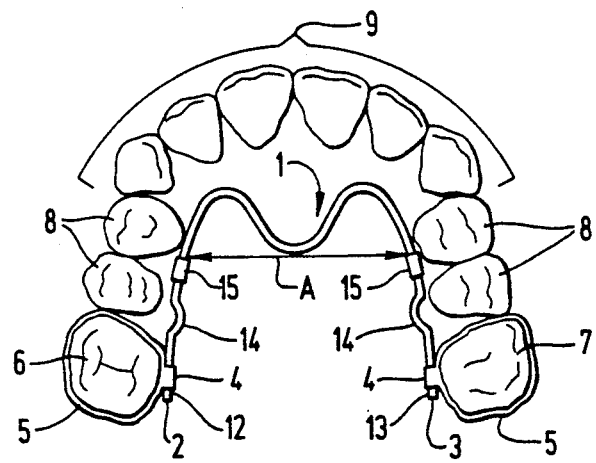
FIG. 3 is an enlarged plan view illustrating the Ni-Ti palatal expansion arch abutting the constricted maligned bicuspids bilaterally and inserted into the lingual sheaths of the mesially, lingually, rotated maxillary first molars.
Figure 4:
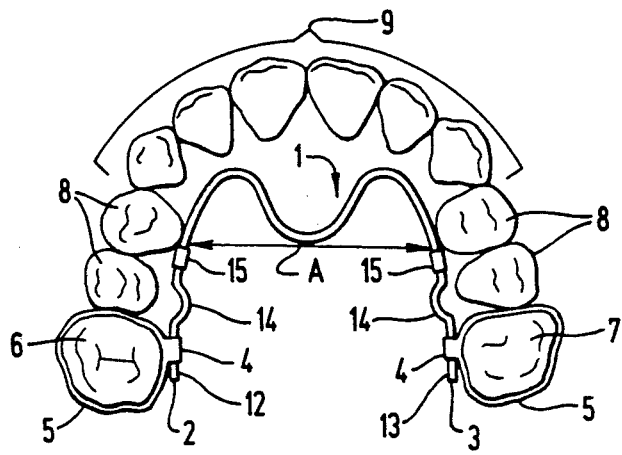
FIG. 4 is a similar plan view showing bilaterally expanded bicuspids and distally rotated maxillary first molars.

Referring now more particularly to FIGS. 2-4, when it is desired to expand the maxillary bicuspids 8, and to rotate the upper first permanent molars 6, 7 to the buccal (in order to make more space for the anterior teeth 9 and thereby permit the latter to assume their proper position during the alignment procedures), the Ni-Ti palatal expansion arch 1 is fitted into sheaths 4 and abutted against bicuspids 8.

The counter-moment force imparted to the Ni-Ti palatal expansion arch expresses itself twenty-four hours a day to produce the changes seen when comparing the arches depicted in FIGS. 3 and 4, and it requires little adjustment by the clinician. As can be appreciated, the degree of rotation, expansion, and torque force imparted to the molars, and the expansion force acting on the bicuspids bilaterally, is directly proportional to the mass and stoichiometric characteristics of the Ni-Ti alloy. Archwire 1 has inherent temperature and memory-retaining characteristics that are a result of a beginning transition temperature from twelve to twenty degrees centigrade.

From time to time, during the course of the palatal alignment and molar arch correction which ordinarily only takes a few months, it may be desirable to change the counter-moment forces acting on the palate. This can be accomplished by increasing the spread dimensions of the "M-shaped" segment of the Ni-Ti arch. This is accomplished by reheating the Ni-Ti alloy segment at 1200 degrees Fahrenheit while under six percent strain. This force adjustment feature is unique in the art when the alloy cools to its martensitic phase it may then be again plastically deformed to the patient's pre-treatment dental arch configuration for easy insertion.

Another force adjustment feature of this invention is the super flexibility of the Ni-Ti maxillary expansion arch in its martensitic phase at ambient temperatures. The archwire possesses a set mechanical characteristic with low mechanical forces in its martensitic phase at ambient and below-mouth temperatures for ease of insertion and when the archwire is subsequently heated by the mouth to a transition temperature, the archwire attempts to return to the initial configuration set in its austenitic phase and applies a greater sustained force when at mouth temperature during treatment until the desired shape or change in palatal width is achieved by the clinician. The nickel-titanium section can also be made from a super elastic grade of Ni-Ti with a minus "0" degrees Fahrenheit T.T.R. This means that the appliance may be distorted and torqued beyond what would be the elastic limit for stainless steel devices and still be inserted effortlessly.

In addition to the rotation of malaligned first permanent molars, in order to position the permanent first molars with the shortest mesial-distal diameter in the maxillary dental arch, thereby eliminating the crowding of the more anterior teeth 9, it frequently occurs that the molars are biased at an angle as shown in FIGS. 5, 7 which requires torquing forces to straighten them. The present invention can also be advantageously utilized for this function without interim treatment adjustments to accomplish the movement. As mentioned, if the roots of upper first permanent molars 6, 7 are deflected outward into the buccal plate of bone as shown in FIG. 5, the rectangular sheaths attached to the molars are biased at the same angle. Upon insertion of lingual sheath inserts 2, 3, the inserts impart forces such that superior members 17 are moved inwardly and inferior members 18 outwardly as shown in FIG. 5. Conversely, if the roots of upper first permanent molars 6, 7 are deflected inwardly into the palatal floor as shown in FIG. 7, rectangular sheaths 4 attached to the molars are biased at the same angle and lingual sheath inserts 2, 3 are turned in such a manner that superior members 17 are moved outwardly and inferior members 18 inwardly as shown in FIG. 7.

One of the features of the present invention is that the temperature and memory-retaining characteristics of the Ni-Ti palatal expansion arch makes possible simultaneous rotation, expansion and torque of the upper first permanent molars, thereby reducing chair time for the clinician as well as providing comfort for the patient. Once the patient's bicuspids 8 have been expanded and the upper first permanent molars 6, 7 have been rotated, expanded intruded and/or torqued into the proper aligned position, archwire 1 can be removed merely by withdrawing end portions 12, 13 from sheaths 4. However, it is advantageous to leave the wire in the patient's mouth for a sufficient period after the desired movement of teeth in order to allow the alveolar bone to stabilize around the roots of the aligned bicuspids and upper first permanent molar.

Once the alveolar bone stabilization has been accomplished, any tendency of the teeth to relapse to their original position is diminished. This is an important feature of the invention since other devices using Ni-Ti wire with memory-retaining characteristics have continued to expand, creating malocclusions. This invention has a self-limiting feature which prevents over expansion. This means the invention may be retained in the maxillary dental arch to stabilize bicuspids and upper first molars during the banding and alignment of the anterior teeth. While it has been mentioned that it ordinarily takes only a few months to expand the bicuspids bilaterally to their proper position, this time frame can vary, depending on such factors as the age, health, anthropology of the patient, lip structure, bone structure, how much pressure is applied and how far the maxillary teeth have been shifted.

A further important characteristic of the Ni-Ti palatal expansion arch 1 is the elimination of unsightly and undesirable face bows used for aligning and extruding the upper first permanent molars. With the present invention, such extrusion of the molars is minimized, thereby further enhancing and facilitating the correction.

From the foregoing detailed description it can be seen that the Ni-Ti removable palatal expansion arch, composed of an alloy with memory-retaining characteristics, is an improvement over the devices heretofore used and is a definite advancement in the art.

In another embodiment of the invention, as depicted in FIGS. 9 and 9A, "M-shaped" archwire 1' is composed of a near-stoichiometric alloy of nickel and titanium as previously described. This embodiment differs from the previously described embodiments in that the Ni-Ti portion of the archwire extends along the palatal arch to the molars and terminates in doubled-over ends 12', 13'. The archwire has length-adjusting loops 14' located approximately at first molars 6', 7'. Lingual sheath inserts 2', 3' are inserted into sheaths 4' so that "M-shaped" archwire 1' is securely mounted as heretofore described. This embodiment eliminates the need for crimped tubes and the use of a second material, such as stainless steel, in the end portions of the archwire. One advantage is that this embodiment comprises a unitary archwire which eliminates the manufacturing step of crimping two pieces of wire together.

Certain changes may be made in embodying the above invention, and in the construction thereof, without departing from the spirit and scope of the invention. It is intended that all matter contained in the above description and shown in the accompanying drawings shall be interpreted as illustrative and not meant in a limiting sense.

It is also to be understood that the following claims are intended to cover all of the generic and specific features of the invention herein described, and all statements of the scope of the invention which, as a matter of language, might be said to fall therebetween.

Particularly, it is to be understood that in the claims, ingredients or compounds recited are intended to include compatible mixtures of such ingredients.

What is claimed is:

1. A method for adjusting the forces imparted on a patient's palatal arch by a temperature-affected archwire comprising:

removing the archwire from the patient's mouth heating the archwire at 1200° Fahrenheit while under 6% strain, deforming the archwire in its martensitic state to the specific configuration of the patient's pre-treated arch, and re-inserting the archwire into the patient's mouth.

2. A method for treatment of a malaligned palatal arch using an archwire composed of a temperature-affected material having a transition temperature below mouth temperature which comprises:

step one: deforming the archwire in its austenitic phase to the specific configuration of a desired post-treatment palatal arch, step two: deforming the archwire in its martensitic state to the specific configuration of a patient's pre-treated malaligned palatal arch, step three: inserting the archwire into the patient's mouth and attaching the ends of the archwire into lingually projecting sheaths, readjusting the forces imparted on the palate by removing the archwire from the patient's mouth, adjusting the archwire spread dimensions and heating the archwire at 1200° Fahrenheit while under 6% strain, repeating steps two and three.

* * * * *